United States Patent
Schermeier et al.

(10) Patent No.: US 9,393,373 B2
(45) Date of Patent: Jul. 19, 2016

(54) PROCESS AND SYSTEM FOR TRANSMITTING MONITORING STATES

(75) Inventors: Olaf Schermeier, Lübeck (DE); Ralf Heesch, Lübeck (DE); Jennifer Lünse, Lübeck (DE); Robert Schmid, Lübeck (DE)

(73) Assignee: Drëgerwerk AG & Co. KGaA., Lübeck (DE)

(*) Notice: Subject to any disclaimer, the term of this patent is extended or adjusted under 35 U.S.C. 154(b) by 2498 days.

(21) Appl. No.: 12/174,009

(22) Filed: Jul. 16, 2008

(65) Prior Publication Data

US 2009/0020123 A1    Jan. 22, 2009

(30) Foreign Application Priority Data

Jul. 20, 2007  (DE) .................. 10 2007 034 018

(51) Int. Cl.
| | |
|---|---|
| *A61M 16/00* | (2006.01) |
| *A61M 16/10* | (2006.01) |
| *G06F 19/00* | (2011.01) |
| *A61M 16/01* | (2006.01) |
| *A61M 16/08* | (2006.01) |

(52) U.S. Cl.
CPC ....... *A61M 16/0051* (2013.01); *G06F 19/3406* (2013.01); *A61M 16/01* (2013.01); *A61M 16/0875* (2013.01); *A61M 2016/0027* (2013.01); *A61M 2016/103* (2013.01); *A61M 2016/1025* (2013.01); *A61M 2016/1035* (2013.01); *A61M 2205/14* (2013.01); *A61M 2205/3553* (2013.01); *A61M 2205/3561* (2013.01); *A61M 2205/3584* (2013.01); *A61M 2205/3592* (2013.01); *A61M 2205/52* (2013.01); *A61M 2205/6018* (2013.01); *A61M 2230/04* (2013.01); *A61M 2230/10* (2013.01); *A61M 2230/205* (2013.01); *A61M 2230/30* (2013.01); *A61M 2230/437* (2013.01); *G06F 19/345* (2013.01)

(58) Field of Classification Search
USPC .................... 128/204.18, 204.21–204.23
See application file for complete search history.

(56) References Cited

U.S. PATENT DOCUMENTS

| | | | | |
|---|---|---|---|---|
| 6,360,745 | B1 * | 3/2002 | Wallace et al. | 128/204.21 |
| 7,225,809 | B1 * | 6/2007 | Bowen et al. | 128/204.21 |
| 7,980,245 | B2 * | 7/2011 | Rice et al. | 128/204.21 |

(Continued)

FOREIGN PATENT DOCUMENTS

| | | |
|---|---|---|
| DE | 19809952 A1 * | 9/1999 |
| EP | 1731089 A1 * | 12/2006 |

*Primary Examiner* — Lynne Anderson
*Assistant Examiner* — Kathryn E Ditmer
(74) *Attorney, Agent, or Firm* — McGlew and Tuttle, P.C.

(57) ABSTRACT

A process and system are provided for transmitting monitoring states between respirators. The process includes the detection of and recording of monitoring states of a monitoring unit (5) of at least a first monitoring period (10) of a first respirator (2). There is an assignment of an identification to the monitoring states of the monitoring unit (5) of the at least first monitoring period (10) of the first respirator (2). There is a transmission of the monitoring states of the monitoring unit (5) of the at least first monitoring period (10) of the first respirator (2) to a second respirator (3). This is followed by a setting of the monitoring unit (5) of the second respirator (3) corresponding to the transmitted monitoring states of the monitoring unit (5) of the at least first monitoring period (10) of the first respirator (2). This is then followed by a repetition of steps for the monitoring states of the monitoring unit (5) of each additional monitoring period (10) of the first respirator (2).

19 Claims, 1 Drawing Sheet

(56) References Cited

U.S. PATENT DOCUMENTS

2005/0133027 A1* 6/2005 Elaz et al. ............... 128/200.24
2006/0278221 A1* 12/2006 Schermeier et al. ..... 128/204.18
2007/0265877 A1* 11/2007 Rice et al. ........................ 705/2
2011/0001611 A1* 1/2011 Schermeier et al. ....... 340/10.51

* cited by examiner

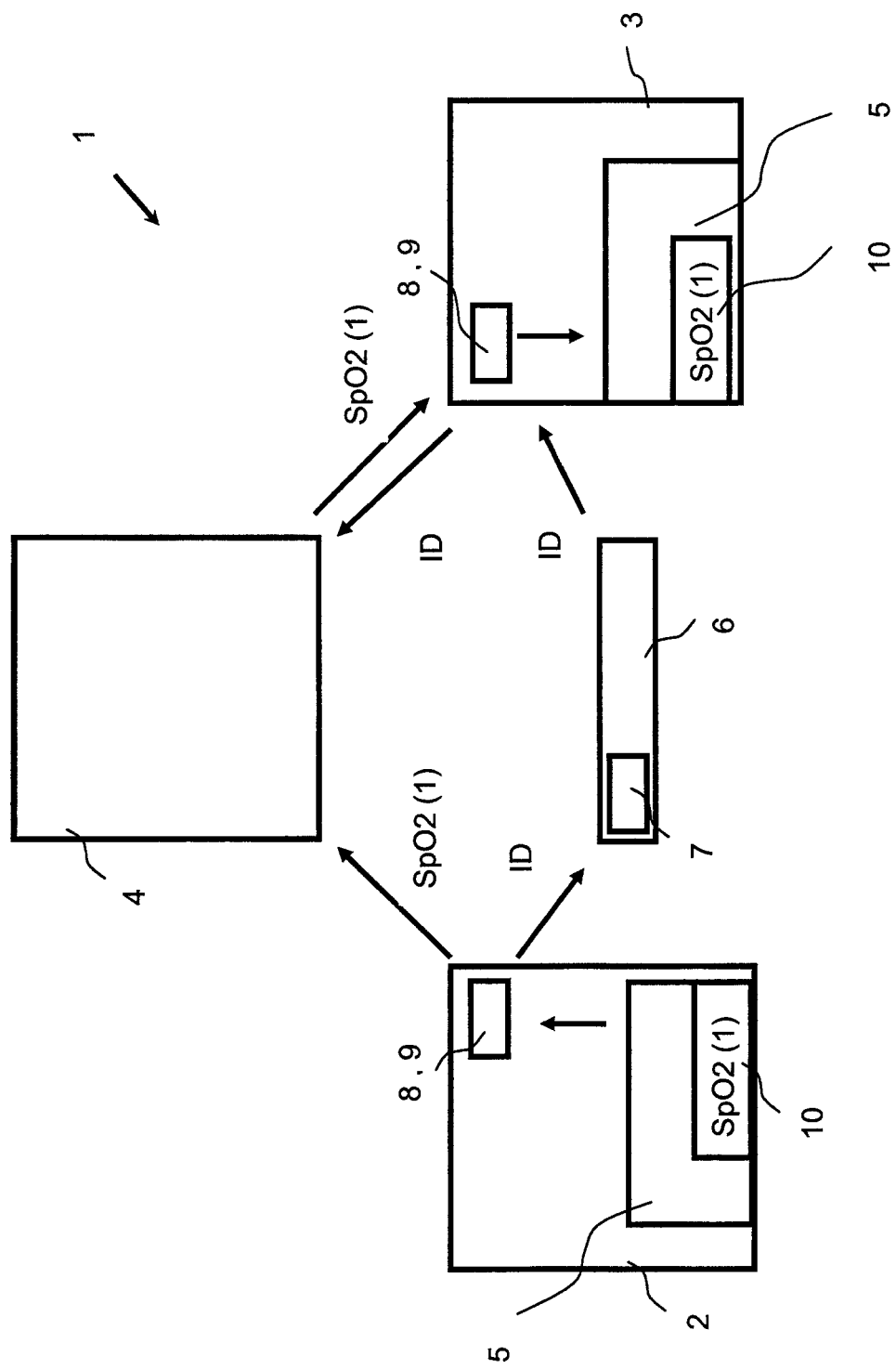

PROCESS AND SYSTEM FOR TRANSMITTING MONITORING STATES

CROSS REFERENCE TO RELATED APPLICATIONS

This application claims the benefit of priority under 35 U.S.C. §119 of German Patent Application DE 10 2007 034 018.6 filed Jul. 20, 2007, the entire contents of which are incorporated herein by reference.

FIELD OF THE INVENTION

The present invention pertains to a process for transmitting monitoring states between respirators.

BACKGROUND OF THE INVENTION

Modern respirators (also known as ventilators) are characterized by increasing complexity of monitoring and supply of the patients. They have monitoring units, which record a great variety of variables, for example, airway pressures, breathing gas concentrations or oxygen saturations of the patient's blood. The monitoring units of the respirators check the measured values within the set limit values and inform the user in case of changes. In more modern respirators, the monitoring units of the respirators are equipped with intelligent algorithms, which automatically recognize whether a certain variable to be monitored shall be monitored. It is detected for this, for example, whether a sensor necessary herefor has been connected to the patient and whether it is providing corresponding measurement results. It is only after all the criteria necessary for monitoring the variable to be monitored have been met that the monitoring unit is activated. If, for example, a patient is connected to a respirator in an ambulance, the oxygen saturation of the blood ($SPO_2$ value) is thus monitored only after a sensor for measuring the $SPO_2$ value of the patient has been connected and the monitoring unit has detected the pulse of the patient. If the patient is connected to another, second respirator after transport into an operating room of a hospital, the $SPO_2$ value is monitored again only when the monitoring unit has recognized a sensor connected to the patient and has recognized a pulse from this patient. However, if the patient's status has considerably exacerbated at the time of the changeover between the respirators or if one has forgotten to connect the pulse monitoring, so that no pulse has been able to be recognized by the monitoring unit, no monitoring of the $SPO_2$ measurement takes place because of the automatic monitoring control. No alarm is triggered for the user for the lack of $SPO_2$ measurement and/or the exacerbated state of the patient. This state may lead to a worsening of the patient's status.

SUMMARY OF THE INVENTION

The basic object of the present invention is to overcome the existing drawbacks of the state of the art.

According to the invention, a process is provided for transmitting monitoring states between respirators. The process comprises:

a) detecting and recording monitoring states of a monitoring unit for an at least first monitoring period of a first respirator;

b) assigning an identification to the monitoring states of the monitoring unit of the at least first monitoring period of the first respirator;

c) transmitting monitoring states of the monitoring unit of the at least first monitoring period of the first respirator to a second respirator;

d) setting a second respirator monitoring unit of the second respirator corresponding to the transmitted monitoring states of the monitoring unit of the at least first monitoring period of the first respirator; and e) repeating the steps a) through d) for monitoring states of the monitoring unit of each additional monitoring period of the first respirator.

According to another aspect of the invention, a system is provided for transmitting monitoring states between respirators. The system comprises a first respirator with a first respirator monitoring unit detecting and recording monitoring states for an at least first monitoring period of the first respirator and assigning an identification to the monitoring states of the monitoring unit of the at least first monitoring period of the first respirator. A second respirator is provided with a second respirator monitoring unit. A transmitting unit is associated with the first respirator for transmitting monitoring states of the monitoring unit of the at least first monitoring period of the first respirator to the second respirator for setting the second respirator monitoring unit of the second respirator corresponding to the transmitted monitoring states of the monitoring unit of the at least first monitoring period of the first respirator. The first respirator monitoring unit repeats the detecting and recording for monitoring states of the monitoring unit of each additional monitoring period of the first respirator and the transmitting unit transmits monitoring states of each additional monitoring period for setting the second respirator monitoring.

The present invention has the essential advantage that when the patient is changed over from a first respirator to a second respirator, the monitoring states of at least one first monitoring period of the first respirator are taken into account for setting the monitoring unit of the second respirator and the risk of both incorrect settings and errors in operation of the respirators are thus minimized and the safety of the patient is thus significantly increased. A monitoring period is a time period for measuring a variable to be monitored.

Besides the data detected in process step a), the identification assigned in process step b) is advantageously also transmitted to a monitoring information system, and the data detected in process step a) are stored with the identification assigned in process step b). The identification assigned in process step b) can be stored on a readable memory element of an accessory, preferably a flexible breathing tube, by a transmitting unit. The flexible breathing tube is connected to the second respirator, and an identification stored on the memory element of the flexible breathing tube can be read by a receiving unit of the second respirator. The monitoring states of the at least first monitoring period of the first respirator can be polled by the second respirator by this identification by means of the monitoring information system and transmitted to the second respirator.

The first respirator, second respirator and monitoring information system are advantageously connected to one another via a network. The first respirator, second respirator and monitoring information system may also be in connection with one another in a wireless manner. When the monitoring unit of the second respirator is set corresponding to the transmitted monitoring states of the monitoring unit of the monitoring period of the first respirator, the current variables to be monitored of the second respirator are advantageously taken into account.

A monitoring state may preferably comprise an activation and/or deactivation of at least one variable to be monitored.

Especially an $SPO_2$ measurement and/or an anesthetic concentration measurement are considered to be variables to be monitored. The activation and/or deactivation of a variable to be monitored of the first respirator is thus recorded and taken into account when setting the monitoring unit of the second respirator.

A device for carrying out the process according to the present invention is shown in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view showing a device for carrying out the process according to the present invention.

DESCRIPTION OF THE PREFERRED EMBODIMENTS

Referring to the drawings in particular, the present invention will be explained in more detail below on the basis of two exemplary embodiments of a respiration system 1.

A monitoring unit 5 detects the monitoring states of a first respirator 2, which supplies a patient located in a preparation room for surgery with breathing gas. An identification is assigned to the monitoring states of a first monitoring period 10. The identification may comprise, for example, the name of the patient, a treatment number or a patient identification number. The monitoring states of the first monitoring period 10 of the first respirator 2 comprise the measured variables and settings of an $SPO_2$ measurement and of a gaseous anesthetic measurement. The first respirator 2 is connected to a monitoring information system 4 via a data network. If the monitoring unit 5 of the first respirator 2 is activated upon recognition of an $SPO_2$ sensor connected to the patient and of the patient's pulse, the monitoring states are transmitted via the data network to the monitoring information system 4. The monitoring states contain data on measured values, an activation of a measurement and the duration of the measurements already carried out. The monitoring states are stored on the monitoring information system 4 under the assigned identification. However, it is advantageously also possible to transmit monitoring states of additional monitoring periods 10 to the monitoring information system 4 and to store them. Two identifications may be assigned for this: A first identification, which characterizes a patient to be monitored, and a second identification, which characterizes the particular monitoring period 10 of the first respirator 2. In addition, a characteristic of the first respirator can be transmitted together with the identifications. The assigned identifications are stored with a transmitting unit 8 of the first respirator 2 on a readable memory element 7. The memory element 7 is preferably located in the sheathing of a flexible breathing tube 6 connected to the first respirator 2. The memory element 7 may, however, also be provided on the outer surface of a flexible breathing tube 6 connected to the first respirator 2.

After the patient has been transported into an operating room, the flexible breathing tube 6 is removed from the first respirator 2 and is connected to a second respirator 3 located in the operating room. The second respirator 3 is now provided with a receiving unit 9 for reading the data stored in the memory element 7 of the flexible breathing tube 6. The second respirator 3 is at the same time connected to the monitoring information system 4 via a network. After reading the identification from the memory element 7, the monitoring states of the first monitoring period 10 of the first respirator 2 can be polled by the second respirator 3 by means of the monitoring information system 4 and transmitted into the second respirator 3. After the transmission is complete, the monitoring state of the first respirator 2 is analyzed by the second respirator 3. The current variables to be monitored of the second respirator 3 are advantageously taken into account for this during the setting of the monitoring unit 5 of the second respirator 3. It can be recognized from the monitoring state of the first respirator 2 for the monitoring unit 5 of the second respirator 3 that an $SPO_2$ measurement and breathing gas monitoring have already taken place at the first respirator 2. If no activation of the $SPO_2$ measurement takes place at the second respirator 3 within a predefined time period based on the recognized $SPO_2$ sensor and the patient's pulse, or an $SPO_2$ measurement fails to provide measured values, a corresponding alarm signal is triggered by the monitoring unit 5 of the second respirator 3. The alarm signal signals to the user that either the $SPO_2$ sensor is not connected to the second respirator 3 and/or to the patient or that no pulse of the patient is being detected, for example, because of a significant worsening of the patient's status during the transportation from the preparation room into the operating room. For example, a non-recognized oxygen deficiency in the arterial blood or in the tissue of the patient (hypoxia) occurs only if the corresponding alarm signal from the second respirator 3 is not noticed by the user. Thus, safety gaps in the monitoring of a patient can be closed effectively with the process according to the present invention.

The variables to be monitored of a monitoring state may comprise a $CO_2$ measurement and/or an $O_2$ measurement. However, the process according to the present invention is not limited to these variables to be monitored alone. The variables to be monitored of a monitoring state may also include, for example, ECG, BIS (bispectral index), EEG, blood pressure signals, a tidal volume, a respiratory pressure, a species of the gaseous anesthetics and/or a depth of anesthesia or hypnosis.

The second exemplary embodiment describes a monitoring unit 5 of a first respirator 2 of a respiration system 1, in which the course of therapy is analyzed as a model at a patient. The limit values to be checked are derived by the monitoring unit 5 from the analysis results. Such monitoring units 5 can be encountered in case of the so-called "awareness prevention" monitoring. The term "awareness" designates the alertness of the patient during an anesthesia. An alert state during anesthesia shall be prevented with "awareness prevention" monitoring. The monitoring unit 5 recognizes from the inspiratory and expiratory measured values obtained for the gaseous anesthetic whether the currently active respirator is the source of the gaseous anesthetic supply for the patient. If it is, the intensity of anesthesia produced by this gaseous anesthetic supply in the patient is analyzed, furthermore, as a model based on the expiratory gaseous anesthetic measured values. If the patient has been brought into a medically relevant state of anesthesia, a certain alarm limit is activated by the monitoring unit 5, and this alarm limit is monitored relative to the state of anesthesia of the patient. If the first respirator 2 sets the gaseous anesthetic supply based on erroneous supply or if it is set conditionally by the user, a warning can be generated by the monitoring unit 5 of the user in time before the patient wakes up. The data of the monitoring state of the "awareness prevention" monitoring are made available by the first respirator 2 to a monitoring information system 4 after a corresponding identification has been assigned. The data can be transmitted, just as in the first exemplary embodiment, via lines, via a network or via a corresponding radio connection. The data are stored on the monitoring information system 4 under the assigned identification. The identification is transmitted by a transmitting unit 8 of the first respirator 2 to a memory element 7 provided in a flexible breathing tube 6. When the patient is changed over to a second respirator 3, for example, during the patient's transfer from the operating room to the intensive care unit, the flexible breathing tube 6 remains at the patient. After the patient has been connected to the second respirator 3, the identification stored in the memory element 7 is detected by a receiving unit 9 of the second respirator 3. The data of the monitoring state of the "awareness prevention" monitoring of the first respirator 2 can be requested by means of this identification by the monitoring information system 4 and transmitted into the second respirator 3. A setting of the "awareness prevention" monitoring is performed at the second respirator 3 on the basis of these data and the current data of the second respirator 3. If values that deviate from the values that were determined by the monitoring unit 5 of the first respirator 2 are now determined by the second respirator 3, an alarm is sent to the user of the second respirator 3.

The monitoring unit 5 of a second respirator 3 can be set optimally for reliable patient monitoring with the process according to the present invention.

While specific embodiments of the invention have been shown and described in detail to illustrate the application of the principles of the invention, it will be understood that the invention may be embodied otherwise without departing from such principles.

APPENDIX

List of Reference Numbers

1 Respiration system
2 First respirator
3 Second respirator
4 Monitoring information system
5 Monitoring unit
6 Flexible breathing tube
7 Memory element
8 Transmitting unit
9 Receiving unit
10 Monitoring period

What is claimed is:

1. A system for transmitting monitoring statuses between breathing apparatuses, the system comprising:
 a first breathing apparatus with a first breathing apparatus monitoring unit detecting and recording monitoring statuses for an at least first monitoring period of said first breathing apparatus and assigning at least one identifier to the monitoring statuses of the at least first monitoring period of said first breathing apparatus monitoring unit of said first breathing apparatus;
 a second breathing apparatus with a second breathing apparatus monitoring unit; and
 a transmitting unit associated with said first breathing apparatus for transmitting monitoring statuses of the at least first monitoring period of said first breathing apparatus monitoring unit of said first breathing apparatus to said second breathing apparatus for setting said second breathing apparatus monitoring unit of said second breathing apparatus corresponding to the transmitted monitoring statuses of the at least first said monitoring period of said first breathing apparatus monitoring unit of said first breathing apparatus, said second breathing apparatus monitoring unit detecting current monitoring statuses of said second breathing apparatus, wherein a deviation of the current monitoring statuses of said second breathing apparatus from the monitoring statuses of the at least first monitoring period of said first breathing apparatus is signaled via said second breathing apparatus.

2. A system in accordance with claim 1, further comprising a monitoring information system wherein together with the identification assigned, the data detected by said first breathing apparatus monitoring unit in detecting monitoring statuses are transmitted to said monitoring information system, wherein the data detected are stored on said monitoring information system based on the identification assigned.

3. A system in accordance with claim 1, wherein data for characterizing the monitoring statuses of said first breathing apparatus monitoring unit of the at least first monitoring period of said first breathing apparatus are stored on a readable memory element, said at least first monitoring period corresponding to a time period for measuring at least one variable.

4. A system in accordance with claim 3, wherein said memory element is provided in an accessory comprising a flexible breathing tube.

5. A system in accordance with claim 1, wherein an alarm is generated when one of an $SPO_2$ measurement does not take place at said second breathing apparatus within a predetermined time period and said $SPO_2$ measurement does not provide measure values after said monitoring statuses of said first breathing apparatus monitoring unit are transmitted to said second breathing apparatus monitoring unit.

6. A method for transmitting monitoring statuses between breathing apparatuses, the method comprising the steps of:
 providing a first breathing apparatus comprising a first monitoring unit;
 providing a second breathing apparatus comprising a second monitoring unit;
 detecting and recording monitoring statuses of at least one monitoring period of said first monitoring unit of said first breathing apparatus;
 assigning an identification to the monitoring statuses of said at least one monitoring period of said first monitoring unit;
 transmitting said at least one identification and said monitoring statuses of said at least one monitoring period of said first monitoring unit of said first breathing apparatus to said second breathing apparatus;
 setting said second monitoring unit of said second breathing apparatus based on the transmitted monitoring statuses of said at least one monitoring period of said first breathing apparatus and present monitoring statuses of said second monitoring unit of said second breathing apparatus; and
 generating a signal with said second breathing apparatus when said present monitoring statuses of said second breathing apparatus deviate from said monitoring statuses of said at least one monitoring period of said first breathing apparatus.

7. A method for transmitting monitoring statuses between breathing apparatuses, the method comprising the steps of:
 a) detecting and recording monitoring statuses of at least one monitoring period of a monitoring unit of a first breathing apparatus;

b) assigning at least one identifier to the monitoring statuses of said at least one monitoring period of said monitoring unit of said first breathing apparatus;

c) transmitting said at least one identifier and said monitoring statuses of said at least one monitoring period of said monitoring unit of said first breathing apparatus to a second breathing apparatus; and d) adjusting a monitoring unit of said second breathing apparatus according to the transmitted monitoring statuses of said at least one monitoring period of said first breathing apparatus, wherein present monitoring statuses of said monitoring unit of said second breathing apparatus are taken into account in adjusting said monitoring unit of said second breathing apparatus such that a deviation of the present monitoring statuses of said second breathing apparatus from said monitoring statuses of said at least one monitoring period of said first breathing apparatus is signaled by said second breathing apparatus.

8. A method in accordance with claim 7, wherein in step b) two identifiers are assigned to the monitoring statuses of the at least one monitoring period of the monitoring unit of the first breathing apparatus, one of said two identifiers identifying the patient and another one of said two identifiers identifying the at least one monitoring period.

9. A method in accordance with claim 8, wherein the monitoring statuses of the at least one monitoring period of the first breathing apparatus are requested from the monitoring information system by the second breathing apparatus under one of the two identifiers and transmitted to the second breathing apparatus.

10. A method in accordance with claim 7, wherein the monitoring statuses of the at least one monitoring period detected in step a) are transmitted to a monitoring information system with the identifier assigned in method step b), the monitoring statuses of the at least one monitoring period detected in step a) being stored at the monitoring information system under the identifier assigned in method step b).

11. A method in accordance with claim 10, wherein said first breathing apparatus, said second breathing apparatus and said monitoring information system are interconnected by means of a data network.

12. A method in accordance with claim 7, wherein data for identification of the monitoring statuses of the at least one monitoring period of the monitoring unit of the first breathing apparatus are stored on a readable memory element.

13. A method in accordance with claim 12, wherein the memory element is provided in an accessory part, said accessory part being formed as a breathing tube.

14. A method in accordance with claim 13, wherein in method step c) the accessory part is connected to the second breathing apparatus, wherein the data of the memory element of the accessory part are read by a receiver unit of the second breathing apparatus.

15. A method in accordance with claim 7, wherein at least one of said monitoring statuses comprises one or more of an activation of at least one monitoring variable and a deactivation of the at least one monitoring variable.

16. A method in accordance with claim 15, wherein the at least one monitoring variable comprises one or more of an $SpO_2$ measurement, a $CO_2$ measurement, an $O_2$ measurement and a measurement of a concentration of an anesthetic.

17. A method in accordance with claim 15, wherein in method step d) one or more of the activation of the at least one monitoring variable and the deactivation of the at least one monitoring variable is taken into account.

18. A method in accordance with claim 7, wherein in method step d) at least one monitoring variable is activated and the activation of the at least one monitoring variable takes place with a time delay.

19. A method in accordance with claim 7, wherein an alarm is generated when one of an $SPO_2$ measurement does not take place at said second breathing apparatus within a predetermined time period and said $SPO_2$ measurement does not provide measure values after said monitoring statuses of said monitoring unit of the at least one monitoring period of said first breathing apparatus are transmitted to said second breathing apparatus.

* * * * *